United States Patent [19]
Code

[11] Patent Number: 5,224,679
[45] Date of Patent: Jul. 6, 1993

[54] NOZZLE HOLSTER

[76] Inventor: William E. Code, 57 Cambridge Cr., Saskatoon, Sask., Canada, S7H 3P9

[21] Appl. No.: 720,151

[22] Filed: Jun. 27, 1991

[30] Foreign Application Priority Data

Jan. 28, 1991 [CA] Canada ................................ 2035060

[51] Int. Cl.⁵ .............................................. A47F 5/00
[52] U.S. Cl. .................................. 248/314; 128/852; 248/313
[58] Field of Search ...................... 248/314, 316.7, 313, 248/101, 231.8; 128/852; 5/503.1, 658; 224/269, 252, 242, 245

[56] References Cited

U.S. PATENT DOCUMENTS

| | | | |
|---|---|---|---|
| 625,752 | 5/1899 | Ford | 248/314 |
| 931,437 | 8/1909 | Larson | 248/314 |
| 1,485,510 | 3/1924 | Kron | 248/314 |
| 1,772,176 | 8/1930 | Benjamin | 248/214 |
| 2,174,140 | 9/1939 | Schofield | 248/224.1 |
| 2,564,389 | 8/1951 | Bochm et al. | 248/314 |
| 2,665,103 | 1/1954 | Flora et al. | 248/314 |
| 2,738,209 | 3/1956 | Brown | 248/314 |
| 3,096,960 | 7/1963 | Kinney | 248/314 |
| 3,777,953 | 12/1973 | Lewis | 224/245 X |
| 4,476,860 | 10/1984 | Collins et al. | 128/852 X |
| 4,597,551 | 7/1986 | Ciechanowski et al. | 248/297.2 X |
| 5,072,868 | 12/1991 | Dickie et al. | 224/269 |

Primary Examiner—Alvin C. Chin-Shue
Assistant Examiner—Korie H. Chan
Attorney, Agent, or Firm—A. N. Sadik

[57] ABSTRACT

A holster for supporting an elongated hand-held instrument, when the instrument is not in use, comprises at least one clip, and a frame, for securing a contamination barrier around the instrument and for allowing the instrument to be inserted into, and withdrawn from, the interior of the barrier; and a support for the frame. The holster is of use for intake nozzles of medical and dental operating room suction equipment.

3 Claims, 3 Drawing Sheets

NOZZLE HOLSTER

BACKGROUND OF THE INVENTION

1. Field of the Invention

This invention pertains to holsters for supporting surgical/medical instruments when not in use. In particular, this invention pertains to holsters for intake nozzles of medical and dental suction equipment, for example, in operating rooms.

2. Description of Related Prior Art

Prior art nozzle holsters include devices such as that shown in U.S. Pat. No. 4,597,551 issued on Jul. 1, 1986 to Ciechanowski et al. That device is for instruments having a flexible tube-like or cord-like extension attached to the nozzle end inserted into the holster (column 1, lines 50 to 52). To accommodate such an instrument the Ciechanowski device comprises an elongated cylindrical shell having an upper end, a lower end and a smoothly tapered longitudinal slot extending from the upper end to near the lower end and a means for attaching the apparatus to a surface in an orientation favourable to the us of the force of gravity to cradle the instrument in the shell against random dislodging forces (column 1, lines 53 to 59). The slot in the Ciechanowski device does not extend the full length of the device. The bottom of the slot cradles the instrument near the point of attachment of the instrument to the tube-like or cord-like extension (column 1, line 59 to column 2, line 5). Even if the Ciechanowski slot had a clip-like function, if one inserted a bubble wrapped instrument in the Ciechanowski device the instrument would tend to slip out of the wrap if the wrap were to fit loosely enough around the instrument to allow for easy insertion and withdrawal of the instrument from the wrap. Contaminants would tend to travel down the instrument to the extension and onto the Ciechanowski device. The Ciechanowski device therefore is susceptible to contamination by the material worked on as a result of the structure, size and configuration of that device.

Prior art nozzle holsters also include two further types of devices having vertical openings therein and which, like the Ciechanowski device, result in a trade-off between preventing contamination and easy insertion and withdrawal of the instrument. One type is an elongated device the opening in which is a groove of substantially C-shaped transverse cross-section for gripping the upper end of the sides of a nozzle. The other type comprises a sheet-like platform having one or more holes there through for the insertion and withdrawal of a nozzle. Nozzles of medical and dental suction equipment are connected to long hoses which tend to pull them from those holsters, resulting in contamination by, or of, the environment around those holsters. Moreover, the openings in each type of these two types of prior art devices are of a size and location only to receive a nozzle alone, not a nozzle having a bubble wrap surrounding it In the alternative to using the above-mentioned prior art devices, medical and dental operating room suction nozzles have sometimes been held, between uses, by being inserted between a cushion below the patient and the operating table. This is unhygienic due to contamination and is generally not satisfactory.

SUMMARY OF THE INVENTION

Since intake nozzles, and the like, for medical and dental operating room suction equipment are normally sealed in sterile bubble wraps by the instrument manufacturers, it is opportune to utilize that existing wrap to prevent contamination.

Further, there is a problem not as to where to store the instrument while it is clean (i.e. not yet contaminated), but rather as to where it should be placed once used for a patient so as to be readily available to be used again on that individual patient. Typically, in anaesthesia such an instrument need be available at the beginning and end of an operation or other medical procedure. It must be immediately and easily accessible with one hand (usually the right) to remove secretions or vomited stomach contents so the patient does not aspirate such materials into the lungs, which can entail major adverse outcomes, even death.

The nozzle holster of the present invention, therefore, secures the bubble wrap to the holster so the residual secretions on the nozzle only touch the patient's disposable instrument and wrapper. At the end of the procedure the wrapper and nozzle can be thrown away and a new instrument and wrapper put in place. Alternatively, a disposable sterilizable liner may be specially adapted to be received and retained in the holster. A clip at the bottom of the holster allows the bubble wrap or liner to stay in place when the instrument is removed, used, and then replaced into the holster. A friction fit holster and/or further clip near the top of the device could also permit this to be achieved. Such a device would have the advantage over prior art devices of confining an individual's secretions to themselves and hence of reducing potential spread of infection (e.g. AIDS & Hepatitis B) between patients, between patients and care givers, and between patients and their environment (e.g. the floor or operating table).

Accordingly, the present invention provides a surgical/medical appliance for attachment to an operating table or the like, comprising: a rigid holster-like shell having a solid continuous interior surface open upper and lower ends; means for attaching said shell to a side of said operating table; said holster-like shell adapted to receive and retain a disposable contamination-barrier sac for containing bodily secretions from a surgical/medical instrument inserted into the sac through its upper, open end between uses of the instrument on a individual patient during a surgical/medical procedure.

The present invention further provides a holster for supporting an elongated hand-held instrument when not in use, comprising a substantially tubular shell having a solid continuous interior surface; means, located on the interior surface of the shell, for receiving and retaining a contamination barrier and retained int he contamination barrier sac; and means for attaching the holster to a side of a table.

BRIEF DESCRIPTION OF THE DRAWINGS

A preferred embodiment of the present invention will now be described with reference to the annexed drawings, wherein.

DESCRIPTION OF PREFERRED EMBODIMENTS

Figure 1:
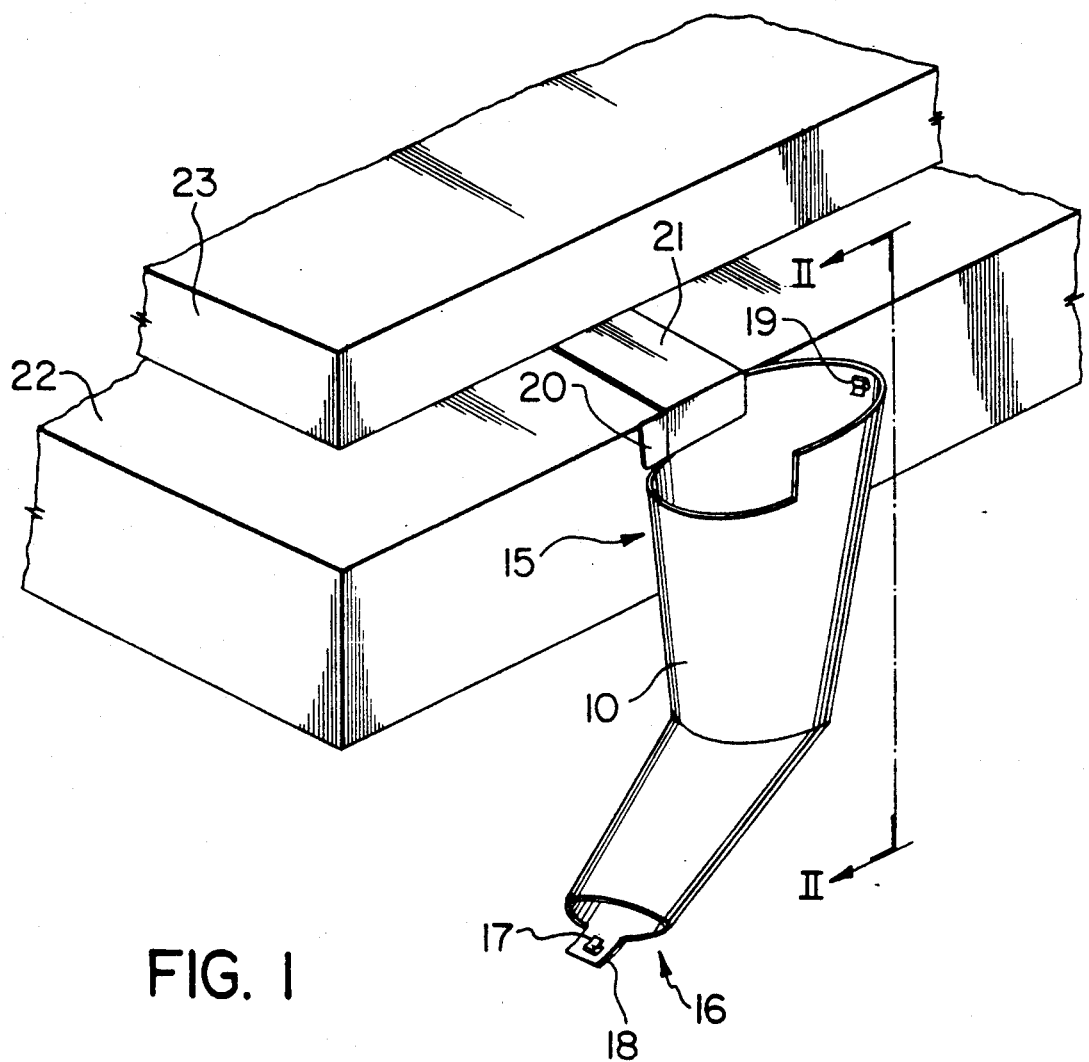
FIG. 1 is a perspective view of a preferred embodiment of the device of the present invention.

Reference now is made in detail to the present preferred embodiments of the invention, examples of which are illustrated in the accompanying drawings, wherein like reference numerals indicate like elements throughout the several views.

FIG. 1 shows a nozzle holster 10 according to the present invention installed in place and ready for use.

Figure 2:
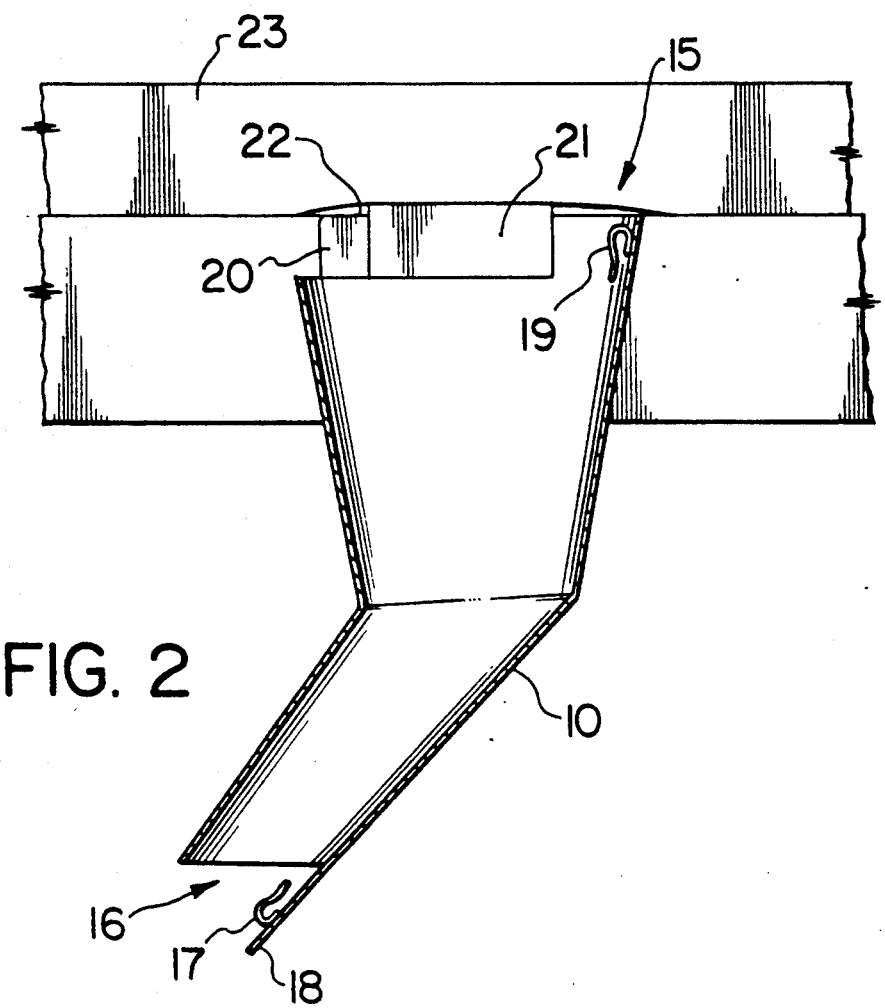
FIG. 2 is a cross-sectional side view along the line II—II in FIG. 1.
Figure 3:
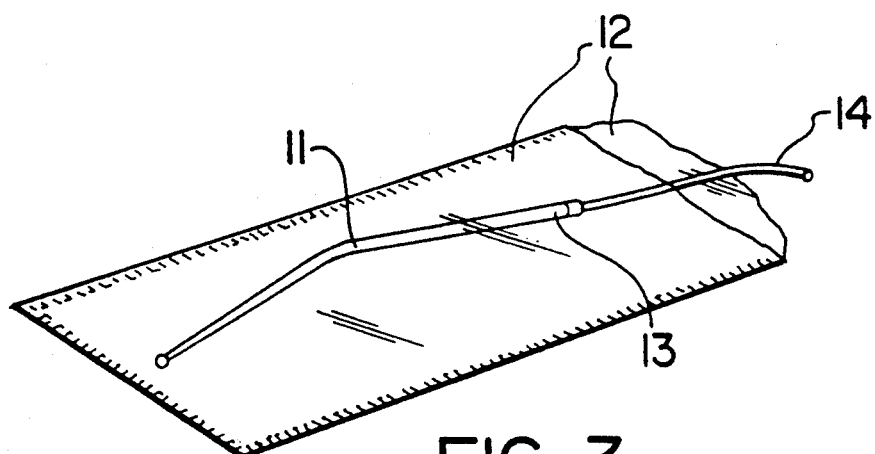
FIG. 3 is a perspective view of a typical instrument for use with the device shown in FIGS. 1 and 2.

With reference also to FIGS. 2 and 3, the body 10 is generally shaped to accommodate an intake nozzle 11 used for medical and dental operating room suction equipment. The nozzle 11 generally arrives in the operating room in sterile condition in a bubble wrap 12 of paper and plastic. The top end of the wrap 12 can be opened so that the upper end 13 of the nozzle 11 can be attached to a suction hose 14.

The holster body 10 is of the same general longitudinal shape as the nozzle 11 but is larger in the transverse direction so that the wrap 12 can be folded around the length of the nozzle 11 so that the wrap 12 and nozzle 11 can be inserted into upper opening 15 of the holster body 10. The holster body 10 also has a lower opening 16 out of which the wrapper 12 and nozzle 11 project and near the lower opening 16 a spring clip 17 on a tab 18 holds the wrap 12 in place. Near the upper opening 15 a clip 19 attached to a collar 20 also holds the wrap 12 in place.

A blade-like arm 21 extends horizontally from near the upper portion of the holster body 10 for insertion between operating room table top 22 and a cushion 23 on the table top 22, thereby attaching the holster 10 to the table. In this preferred embodiment the plane of the blade-like arm 21 is nearly perpendicular to the longitudinal axis of the upper portion of the holster body 10.

The parts for the holster are preferably made of plastic for example by injection moulding. However, a prototype of the holster as shown was made of sheet tin. The two component pieces were sheared from the sheet tin and formed into the blade-like arm 21 and the holster body 10, by conventional means.

The blade-like arm 21 shown was originally a rectangular piece. An end portion of the ar 21 was then bent so as to be perpendicular to the remainder of the arm 21. An L shaped piece resulted.

It is not essential that a cylindrical tube be formed. A somewhat conical tube, as shown in FIGS. 1 and 2, is actually preferred if such shape facilitates the use of the device One of the branches of the blade-like arm 21 is then fastened by fasteners, such as screws or rivets (not shown), to the collar 20 of the top of the holster body 10. The branch of the blade-like arm 21 extending away from the holster body 10 (i.e. "the blade") is preferably arranged to be substantially flush with the top of the holster body 10. The clip 19 is then fastened to the portion of the ar 21 inside the body 10.

Figure 4:
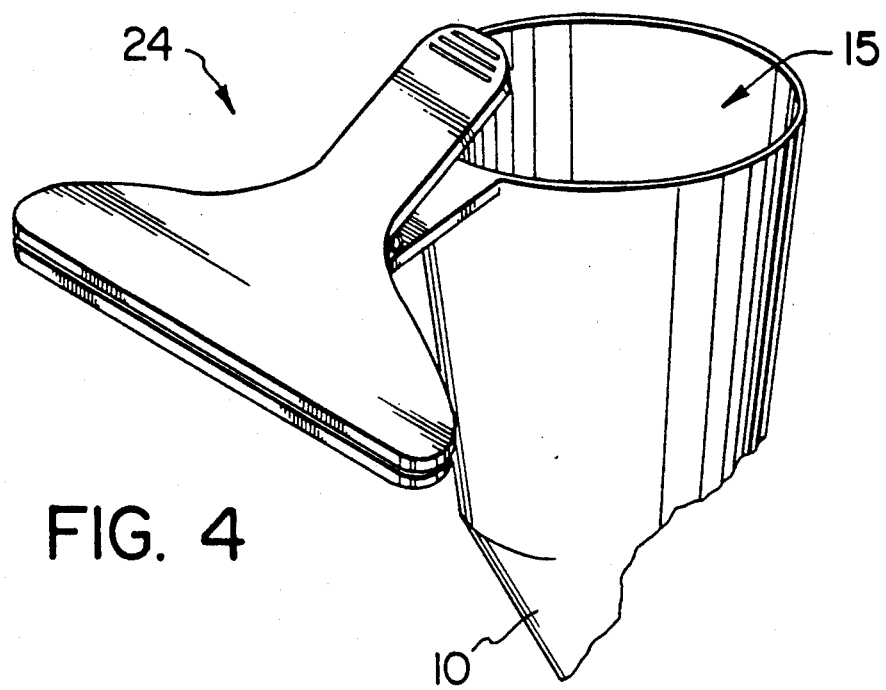
FIG. 4 is a perspective view of a spring-loaded clamp and holster embodiment of the present invention.
Figure 5:
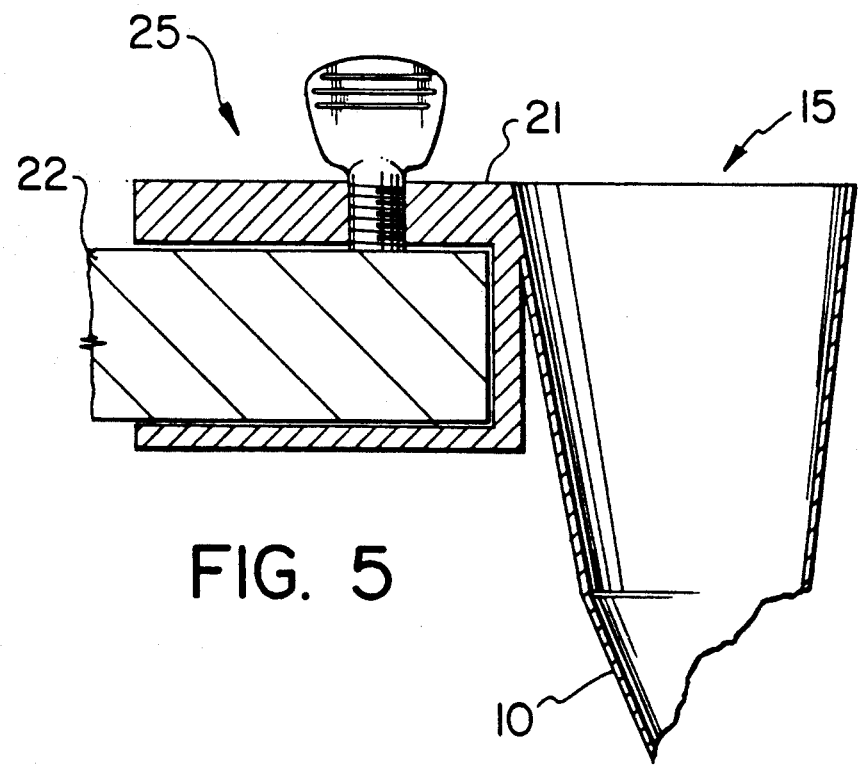
FIG. 5 is a cross sectional side view of a threaded clamp and holster embodiment of the present invention.

Instead of the blade-like arm 21, other means for attaching the holster 10 to a support may be used, such as a spring loaded clamp 24 (FIG. 4) or a threaded C-shaped clamp 25 (FIG. 5).

Care should be taken avoid any sharp points or edges in the holster body 10 or attachments, which might perforate or tear the instrument wrap 12.

It will be apparent to those skilled in the art that various modifications can be made to the nozzle holster of the instant invention without departing from the scope or spirit of the invention, and it is intended that the present invention cover modifications and variations of the nozzle holster provided they come in the scope of the appended claims and their equivalents.

I claim:

1. A surgical/medical appliance for attachment to an operating table or the like, comprising:
   a rigid holster-like shell having a solid continuous interior surface, an open upper end, and an open lower end;
   means for attaching said holster-like shell to a side of said operating table; and
   a disposable contamination-barrier sac to contain bodily secretions removably retained inside said holster-like shell;
   first retaining means, located on the interior surface of said holster-like shell, for engaging and holding said disposable contamination-barrier sac at the lower end of said holster-like shell; and
   second retaining means, located on the interior surface of said holster-like shell, for engaging and holding said disposable contamination-barrier sac of the upper end of said holster-like shell;
   wherein said disposable contamination-barrier sac in said holster-like shell, attached to said operating table by said attaching means, contains bodily secretions form a surgical/medical instrument inserted into said disposable contamination-barrier sac through the upper end of said holster-like shell between uses of the instrument on an individual patient during a surgical/medical procedure.

2. The surgical/medical appliance as claimed in claim 1, wherein said holster-like shell is generally conical and said holster-like shell has the upper end wider than the lower end.

3. The surgical/medical appliance as claimed in claim 2, said shell having a generally arcuate shape along its length.

* * * * *